United States Patent
Slager (10) Patent No.: US 8,901,092 B2
(45) Date of Patent: *Dec. 2, 2014

(54) FUNCTIONALIZED POLYSACCHARIDES FOR ACTIVE AGENT DELIVERY

(75) Inventor: Joram Slager, St. Louis Park, MN (US)

(73) Assignee: SurModics, Inc., Eden Prairie, MN (US)

( * ) Notice: Subject to any disclaimer, the term of this patent is extended or adjusted under 35 U.S.C. 154(b) by 145 days.

This patent is subject to a terminal disclaimer.

(21) Appl. No.: 13/335,724

(22) Filed: Dec. 22, 2011

(65) Prior Publication Data

US 2012/0190726 A1    Jul. 26, 2012

Related U.S. Application Data

(60) Provisional application No. 61/428,130, filed on Dec. 29, 2010.

(51) Int. Cl.
| | |
|---|---|
| *A01N 43/04* | (2006.01) |
| *A61K 31/70* | (2006.01) |
| *A61K 31/713* | (2006.01) |
| *C08B 37/00* | (2006.01) |
| *A61K 31/7088* | (2006.01) |
| *C08L 5/00* | (2006.01) |
| *C12N 15/87* | (2006.01) |
| *A61K 48/00* | (2006.01) |

(52) U.S. Cl.
CPC ............ *A61K 31/7088* (2013.01); *A61K 31/713* (2013.01); *C08B 37/0009* (2013.01); *A61K 48/00* (2013.01); *C08L 5/00* (2013.01); *C12N 15/87* (2013.01)
USPC .................. 514/43; 514/42; 514/45; 514/49; 514/54; 536/22.1; 536/23.1; 536/123.1; 536/123.12

(58) Field of Classification Search
None
See application file for complete search history.

(56) References Cited

U.S. PATENT DOCUMENTS

| | | | |
|---|---|---|---|
| 2,668,156 A | 2/1954 | Caldwell et al. | |
| 4,060,506 A | 11/1977 | Verbanac | |
| 4,079,025 A | 3/1978 | Young et al. | |
| 4,638,045 A | 1/1987 | Kohn et al. | |
| 5,116,927 A | 5/1992 | Floyd et al. | |
| 5,160,745 A | 11/1992 | DeLuca et al. | |
| 5,272,181 A | 12/1993 | Boehmer et al. | |
| 5,407,609 A | 4/1995 | Tice et al. | |
| 5,414,075 A | 5/1995 | Swan et al. | |
| 5,466,233 A | 11/1995 | Weiner et al. | |
| 5,488,102 A | 1/1996 | Vetter | |
| 5,514,379 A | 5/1996 | Weissleder et al. | |
| 5,563,056 A | 10/1996 | Swan et al. | |
| 5,589,577 A | 12/1996 | Peltonen et al. | |
| 5,626,863 A | 5/1997 | Hubbell et al. | |
| 5,668,193 A | 9/1997 | Gouda et al. | |
| 5,705,270 A * | 1/1998 | Soon-Shiong et al. | .... 428/402.2 |
| 5,714,360 A | 2/1998 | Swan et al. | |
| 5,733,994 A | 3/1998 | Koepff et al. | |
| 5,736,371 A | 4/1998 | Samain et al. | |
| 5,770,229 A | 6/1998 | Tanihara et al. | |
| 5,773,021 A | 6/1998 | Gurtler et al. | |
| 5,837,747 A | 11/1998 | Soon-Shiong et al. | |
| 5,866,165 A | 2/1999 | Liu et al. | |
| 5,866,619 A | 2/1999 | Sintov et al. | |
| 5,879,707 A | 3/1999 | Cartilier et al. | |
| 5,885,615 A | 3/1999 | Chouinard et al. | |
| 5,980,948 A | 11/1999 | Goedemoed et al. | |
| 5,993,530 A | 11/1999 | Tanaka et al. | |
| 6,001,395 A | 12/1999 | Coombes et al. | |
| 6,007,833 A | 12/1999 | Chudzik et al. | |
| 6,073,040 A | 6/2000 | Kiyuna | |
| 6,077,698 A | 6/2000 | Swan et al. | |
| 6,156,345 A | 12/2000 | Chudzik et al. | |
| 6,197,757 B1 | 3/2001 | Perrier et al. | |
| 6,277,899 B1 | 8/2001 | Bastioli et al. | |
| 6,303,148 B1 | 10/2001 | Hennink et al. | |
| 6,346,263 B1 | 2/2002 | Mercier et al. | |
| 6,388,047 B1 | 5/2002 | Won et al. | |
| 6,410,044 B1 | 6/2002 | Chudzik et al. | |

(Continued)

FOREIGN PATENT DOCUMENTS

| | | |
|---|---|---|
| EP | 0405917 | 1/1991 |
| EP | 1060741 | 9/2003 |

(Continued)

OTHER PUBLICATIONS

Tseng et al. Advanced Drug Delivery Reviews (2009), vol. 61, pp. 721-731.*

(Continued)

*Primary Examiner* — Patrick Lewis
(74) *Attorney, Agent, or Firm* — Pauly, DeVries, Smith & Deffner, LLC (57) ABSTRACT

Embodiments of the invention include functionalized polysaccharides and compositions and structures including the same. In an embodiment, the invention includes an active agent delivery composition including a polysaccharide functionalized with a coupling group, wherein the polysaccharide lacks charged groups at a pH of between 6 and 8; and a complex comprising a nucleic acid and a transfection agent. In an embodiment, the invention includes an active agent delivery structure including a matrix comprising a polysaccharide covalently cross-linked through the residue of a coupling group on the polysaccharide, the polysaccharide lacking charged groups at a pH of between 6 and 8; and a nucleic acid delivery complex disposed within the active agent delivery structure. In an embodiment, the invention includes a material for medical applications including glycogen functionalized with coupling groups at a degree of substitution of between about 0.01 and 0.5. Other embodiments are also included herein.

20 Claims, 4 Drawing Sheets

(56) References Cited

U.S. PATENT DOCUMENTS

| | | |
|---|---|---|
| 6,410,517 B1 | 6/2002 | Truong et al. |
| 6,419,957 B1 | 7/2002 | Lenaerts et al. |
| 6,514,734 B1 | 2/2003 | Clapper et al. |
| 6,583,219 B2 | 6/2003 | Won et al. |
| 6,586,493 B1 | 7/2003 | Massia et al. |
| 6,596,699 B2 | 7/2003 | Zamora et al. |
| 6,596,860 B1 | 7/2003 | Kesselmans et al. |
| 6,613,563 B1 | 9/2003 | Sosnowski et al. |
| 6,660,827 B2 | 12/2003 | Loomis et al. |
| 6,703,040 B2 | 3/2004 | Katsarava et al. |
| 6,703,048 B1 | 3/2004 | Bengs et al. |
| 6,706,288 B2 | 3/2004 | Gustavsson et al. |
| 6,709,668 B2 | 3/2004 | Won et al. |
| 6,716,445 B2 | 4/2004 | Won et al. |
| 6,719,750 B2 | 4/2004 | Varner et al. |
| 6,748,954 B2 | 6/2004 | Lee et al. |
| 6,770,740 B1 | 8/2004 | Rice et al. |
| 6,846,809 B2 | 1/2005 | Cristiano et al. |
| 6,916,857 B2 | 7/2005 | Won et al. |
| 6,924,370 B2 | 8/2005 | Chudzik et al. |
| 7,025,990 B2 | 4/2006 | Sawhney |
| 7,030,097 B1 | 4/2006 | Saltzman et al. |
| 7,094,418 B2 | 8/2006 | Chudzik et al. |
| 7,138,132 B2 | 11/2006 | Won et al. |
| 7,247,288 B2 | 7/2007 | Kumta et al. |
| 7,514,530 B2 | 4/2009 | Divita et al. |
| 7,531,191 B2 | 5/2009 | Zion et al. |
| 7,638,344 B2 | 12/2009 | Slager et al. |
| 7,759,316 B2 | 7/2010 | Kitamura et al. |
| 2001/0018072 A1 | 8/2001 | Unger |
| 2003/0014036 A1 | 1/2003 | Varner et al. |
| 2003/0215649 A1 | 11/2003 | Jelle |
| 2003/0218130 A1 | 11/2003 | Boschetti et al. |
| 2004/0062778 A1 | 4/2004 | Shefer et al. |
| 2004/0091605 A1 | 5/2004 | Bayer et al. |
| 2004/0133155 A1 | 7/2004 | Varner et al. |
| 2005/0019371 A1 | 1/2005 | Anderson et al. |
| 2005/0025797 A1 | 2/2005 | Wang et al. |
| 2005/0059956 A1 | 3/2005 | Varner et al. |
| 2005/0143363 A1 | 6/2005 | De Juan et al. |
| 2005/0255142 A1 | 11/2005 | Chudzik et al. |
| 2005/0271703 A1 | 12/2005 | Anderson et al. |
| 2005/0271706 A1 | 12/2005 | Anderson et al. |
| 2005/0276837 A1 | 12/2005 | Anderson et al. |
| 2005/0281781 A1 | 12/2005 | Ostroff |
| 2005/0281863 A1 | 12/2005 | Anderson et al. |
| 2005/0287188 A1 | 12/2005 | Anderson et al. |
| 2006/0036029 A1 | 2/2006 | Tomko et al. |
| 2006/0110428 A1 | 5/2006 | De Juan et al. |
| 2006/0286071 A1 | 12/2006 | Epstein et al. |
| 2007/0026037 A1 | 2/2007 | Kloke et al. |
| 2007/0065481 A1 | 3/2007 | Chudzik et al. |
| 2007/0065482 A1 | 3/2007 | Chudzik et al. |
| 2007/0065483 A1 | 3/2007 | Chudzik et al. |
| 2007/0065484 A1 | 3/2007 | Chudzik et al. |
| 2007/0128343 A1 | 6/2007 | Chappa |
| 2007/0155906 A1 | 7/2007 | Hissink et al. |
| 2007/0218102 A1 | 9/2007 | Chudzik et al. |
| 2007/0224247 A1 | 9/2007 | Chudzik et al. |
| 2007/0260054 A1 | 11/2007 | Chudzik |
| 2008/0038354 A1 | 2/2008 | Slager et al. |
| 2008/0089923 A1 | 4/2008 | Burkstrand |
| 2008/0154241 A1 | 6/2008 | Burkstrand et al. |
| 2008/0234183 A1 | 9/2008 | Hallbrink et al. |
| 2009/0093026 A1 | 4/2009 | Dowdy et al. |
| 2009/0124535 A1 | 5/2009 | Markland et al. |
| 2009/0186059 A1 | 7/2009 | Johnson et al. |
| 2009/0214619 A1 | 8/2009 | Reiff |
| 2009/0280181 A1 | 11/2009 | Slager |
| 2009/0304798 A1 | 12/2009 | Davis |
| 2010/0226960 A1 | 9/2010 | Chudzik et al. |
| 2011/0159098 A1 | 6/2011 | Slager et al. |
| 2011/0319473 A1 | 12/2011 | McGonigle et al. |

FOREIGN PATENT DOCUMENTS

| | | |
|---|---|---|
| WO | 9309176 | 5/1993 |
| WO | 9704011 | 2/1997 |
| WO | 00/00487 | 2/2000 |
| WO | 0012616 | 3/2000 |
| WO | 0041647 | 7/2000 |
| WO | 00/05005 | 8/2000 |
| WO | 2004009664 | 1/2004 |
| WO | 2005034875 | 4/2005 |
| WO | 2005072703 | 8/2005 |
| WO | 2005112894 | 12/2005 |
| WO | 2005113034 | 12/2005 |
| WO | 2006071110 | 7/2006 |
| WO | 2007084418 | 7/2007 |
| WO | 2008003043 | 1/2008 |
| WO | 2008019346 | 2/2008 |
| WO | 09/05709 | 1/2009 |
| WO | 2009005709 | 1/2009 |
| WO | 2009043158 | 4/2009 |
| WO | 2009091812 | 7/2009 |
| WO | 2009137689 | 11/2009 |
| WO | 2012006169 | 1/2012 |

OTHER PUBLICATIONS

"Freeze drying," http://en.wikipedia.org/wiki/Freeze_drying, from Wikipedia, May 24, 2010, 6 pages.

International Preliminary Report on Patentability for PCT/US2011/042398, mailed Jan. 8, 2013, 8 pages.

Non-Final Office Action, mailed Nov. 23, 2012 in co-pending U.S. Appl. No. 13/171,171, "Compositions and Methods for Enhancement of Nucleic Acid Delivery," 10 pages.

PCT International Search Report and Written Opinion from International Application No. PCT/US2011/042398, corresponding to U.S. Patent mailed Jul. 30, 2012, pp. 1-15.

"The Science and Practice of Pharmacy," Remington, 21st Edition, Copyright 2006, 14 pages.

Andersen et al., "Delivery of siRNA from lyophlolized polymeric surfaces," Biomaterials, 29 (2008), pp. 506-512.

Artursson et al., "Characterization of Polyacryl Starch Microparticles as Carriers for Proteins and Drugs," J Pharm Sci. Nov. 1984;73(11), pp. 1507-1513.

Azevedo et al., "In Vitro Assessment of the Enzymatic Degradation of Several Starch Based Biomaterials,"Biomacromolecules. Nov.-Dec. 2003;4(6), pp. 1703-1712.

Corveleyn et al., "Maltodextrins as lyoprotectants in the lyophilization of a model protein, LDH," Abstract only, http://www.biomedsearch.com/nih/maltodextrins-as-lyoprotectants-in-lyophilization/8668, accessed May 24, 2010, 2 pages.

Gonnissen et al., "Effect of maltodextrin and superdisintegrant in directly compressible powder mixtures prepared via co-spray drying", European Journal of Pharmaceutics and Biopharmaceutics, vol. 68, issue 2 (Feb. 2008), pp. 277-282.

Hinrichs et al., "The choice of a suitable oligosaccharide to prevent aggregation of PEGylated nanoparticles during freeze thawing and freeze drying,"International Journal of Pharmaceutics, vol. 311. No. 1-2, Mar. 27, 2006, pp. 237-244.

Hinrichs et al., Abstract of "Inulin is a promising cryo-and lyoprotectant for PEGylated lipoplexes", Journal of Controlled Release, vol. 103, Issue 2, Mar. 21, 2005, pp. 465-479, 3 pages.

Hirsch-Lerner et al., "Effect of "helper lipid" on lipoplex electrostatics," Biochim Biophys Acta, Aug. 15, 2005; 1714(2):71-84, Abstract only, 1 page.

Hoare et al., "Hydrogels in drug deliver: Progress and challenges", ScienceDirect, Polymer 49 (2008) pp. 1993-2007.

MacLachlan, "Liposomal Formulations for Nucleic Acid Delivery", Antisense Drug Technologies: Principles, Strategies, and Applications, Second Edition, Taylor & Francis Group, L.L.C., (2007), pp. 237-270.

Maitani et al., "Effect of sugars on storage stability of lyophilized liposome/DNA complexes with high transfection efficiency," International Journal of Pharmaceutics, ScienceDirect, vol. 356, 2008, pp. 69-75.

(56) References Cited

OTHER PUBLICATIONS

Murdan, "A review of pluronic lecithin organogel as a topical and transdermal drug delivery system," *Hospital Pharmacist*, Jul./Aug. 2005, vol. 12, pp. 267-270.
Odian, "Principles of Polymerization", Second Edition, John Wiley & Sons, (1981), pp. 201-204.
Seville et al., "Preparation of dry powder dispersions for non-viral gene delivery by freeze-drying and spray-drying," *The Journal of Gene Medicine*, vol. 4, No. 4, Jul. 1, 2002, pp. 428-437.
Vintiloiu et al., "Organogels and their use in drug deliver—A review," *Journal of Controlled Release*, vol. 125, Issue 3, Abstract only, Feb. 2008, 3 pages.
Yadava et al., "Effect of Lyophilization and Freeze-thawing on the Stability of siRNA-liposome Complexes," *AAPS PharmSciTech*, vol. 9, No. 2, Jun. 2008, pp. 335-341.
Adami, R. C. et al., "Metabolic Stability of Glutaraldehyde Crosslinked Peptide DNA Condensates", J. Pharm. Sci., 88(8), 739-46 Abstract only Aug. 1999.
Akhtar, Saghir et al., "Nonviral Delivery of Synthetic siRNAs in Vivo", The Journal of Clinical Investigation, vol. 117, No. 12 http://www.jci.org Dec. 2007, 3623-3632.
Bergen, Jamie M. et al., "Nonviral Approaches for Neuronal Delivery of Nucleic Acids", Pharmaceutical Research, vol. 25, No. 5 May 2008, 983-998.
Boussif, et al., "A Versatile Vector for Gene and Oligonucleotide Transfer into Cells in Culture and in Vivo: Polyethylenimine", Proc. Natl. Acad. Sci. USA, 92:7297-7301 (1995).
Brandup, et al., "Polymer Handbook", 4th ed. John Wiley & Sons, N.Y. Beginning at VII 1999, pp. 675-710.
Carlisle, et al., "Polymer-Coated Polyethylenimine/DNA Complexes Designed for Triggered Activation by intracellular reduction", The Journal of Gene Medicine, 6:337-344 (2004).
Davis "Non-Viral Gene Delivery Systems", Current Opinion in Biotechnology, 13:128-131 (2002).
Final Office Action Received, Citation mailed Apr. 11, 2012 in co-pending U.S. Appl. No. 12/437,287, "Delivery of Nucleic Acid Complexes From Particles" (12 pages), 12.
Final Office Action, for U.S. Appl. No. 12/968,365, dated Jan. 30, 2013, 9 pages.
First Office Action, from JP Application No. 2011-508670, mailed Nov. 12, 2013 (9 pages).
Godbey, et al., "Tracking the Intracellular Path of Poly(ethylenimine)/DNA Complexes for Gene Delivery", Proc. Natl. Acad. Sci. USA, 96:5177-5181 (1999).
Hatefi, A. et al., "Adenoviral Gene Delivery to Solid Tumors by Recombinant Silk-Elastinlike Protein Polymers", Pharmaceutical Research, vol. 24, 2007, pp. 773-779.
Heath, et al., "Varying Polymer Architecture to Deliver Drugs", The AAPS Journal, 9(2):E235-E240 (2007).
Howard, Kenneth A. et al., "Formulation of a microparticle carrier for oral polyplex-based DNA vaccines", Biochimica et Biophysica Acta 1674 2004, 149-157.
International Preliminary Report on Patentability, from International Application No. PCT/US2009/030972, (our file 1001.517WOU1), mailed Jul. 20, 2010, pp. 1-10.
International Search Report and Written Opinion, from International Application No. PCT/US2009/030972, mailed Apr. 7, 2010, pp. 1-16.
Jang, et al., "Gene Delivery from Polymer Scaffolds for Tissue Engineering", Expert Rev. Medical Devices, 1(1):127-138 (2004).
Jewell, et al., "Release of Plasmid DNA from Intravascular Stents Coated with Ultrathin Multilayered Polyelectrolyte Films", Biomacromolecules, 7:2483-2491 (2006).
Lee, Sungmun et al., "Solid Polymeric Microparticles Enhance the Delivery of siRNA to Macrophages in Vivo", Nucleic Acids Research, 1-10 Nucleic Acids Research Advance Access Sep. 25, 2009, pp. 1-10.
Lucius, et al., "Structure of Transfection-Active Histone H1/DNA Complexes", Molecular Biology Reports, 28:157-165 (2002).

Lungwitz, et al., "Polyethylenimine-Based Non-Viral Gene Delivery Systems", European Journal of Pharmaceutics and Biopharmaceutics, 60:247-266 (2005).
Luu, et al., "Development of a Nanostructured DNA Delivery Scaffold Via Electrospinning of PLGA and PLA-PEG Block Copolymers", Journal of Controlled Release, 89:341-353 (2003).
Mayer, Christian R. et al., "Ultrasound Targeted Microbubble Destruction for Drug and Gene Delivery", Exeort Opin. Drug Deliv. vol. 5(10), 2008, pp. 1121-1138.
Meade, Bryan R. et al., "Enhancing the Cellular Uptake of siRNA Duplexes Following Noncovalent Packaging with Protein Transduction Domain Peptides", Adv Drug Deliv Rev, 60(4-5): 530-536, Abstract Howard Hughes Medical Institute, Author Manuscript Mar. 1, 2008, pp. 1-12.
Moffatt, et al., "PEGylated J591 mAb Loaded in PLGA-PEG-PLGA Tri-Block Copolymer for Targeted Delivery: In Vitro Evaluation in Human Prostrate Cancer Cells", International Journal of Pharmaceutics, 317:10-13 (2006).
Noguchi, Hirofumi et al., "Protein Transduction Technology: A Novel Therapeutic Perspective", Acta Med. Okayama, vol. 60, No. 1 http://www.lib.okayama-u.ac.jp/www/acta/ 2006, pp. 1-11.
"Non-Final Office Action Received", mailed Dec. 1, 2011 in co-pending Application Serial No. 12437287, "Delivery of Nucleic Acid Complexes From Particles" (11 pages), 11.
"Non-Final Office Action", for U.S. Appl. No. 12/437,287, mailed Oct. 8, 2013 (20 pages).
"Non-Final Office Action", from U.S. Appl. No. 12/353,792, mailed Aug. 5, 2010, 17 pages.
"Non Final Office Action", mailed Aug. 9, 2012 in U.S. Appl. No. 12/968,365, "Stabilization and Delivery of Nucleic Acid Complexes," (22 pages).
"Non-Final Office Action", mailed Feb. 11, 2011, in U.S. Appl. No. 12/353,792, (14 pages).
"Notice of Allowance", for U.S. Appl. No. 12/437,287, mailed Mar. 7, 2014, (12 pages).
Oh, et al., "Prolonged Organ Retention and Safety of Plasmid DNA Administered in Polyethylenimine Complexes", Gene Therapy, 8:1587-1592 (2001).
Pannier, et al., "Controlled Release Systems for DNA Delivery", Molecular Therapy, 10(1):19-26 (2004).
Putnam "Polymers for Gene Delivery Across Length Scales", Nature Materials, 5:439-451 (2006).
Quick, et al., "DNA Delivery from Photocrosslinked PEG Hydrogels: Encapsulation Efficiency, Release Profiles, and DNA Quality", J. Control. Release, vol. 96, No. 2 2004, 341-351 Pgs.
Remaut, K. et al., "Nucleic Acid Delivery: Where Material Sciences and Bio-Sciences Meet", Materials Science and Engineering R: Reports, Elsevier, Nov. 7, 2007, vol. 58, No. 3-5, pp. 117-161.
Response to Final Office Action for U.S. Appl. No. 12/437,287, mailed Apr. 11, 2012 (6 pages).
Response to Non-Final Office Action, for U.S. Appl. No. 12/437,287, mailed Oct. 8, 2013 (5 pages).
Response to Restriction Requirement, Filed on Sep. 2, 2011 in co-pending U.S. Appl. No. 12/437,287, "Delivery of Nucleic Acid Complexes From Particles" (1 pages), 1 pgs.
Restriction Requirement Received, mailed Sep. 2, 2011 in co pending U.S. Appl. No. 12/437,287, "Delivery of Nucleic Acid Complexes From Particles" (9 pages), 9 Pgs.
Restriction Requirement, mailed May 25, 2012 in co-pending U.S. Appl. No. 12/968,365, "Stabilization and Delivery of Nucleic Acid Complexes" (6 pages).
Saul, Justin M. et al., "Delivery of Non-Viral Gene Carriers from Sphere-Templated Fibrin Scaffolds for Sustained Transgene Expression", Biomaterials (2007), doi:10.1016/j.biomaterials.2007.07.026 Jul. 26, 2007, 1-12.
Schiffelers, et al., "Cancer siRNA Therapy by Tumor Selective Delivery with Ligand-Targeted Sterically Stabilized Nanoparticle", Nucleic Acids Research, 32(19):e149 (2004).
Schiffelers, et al., "Transporting Silence: Design of Carriers for siRNA to Angiogenic Endothelium", Journal of Controlled Release, 109:5-14 (2005).

(56) References Cited

OTHER PUBLICATIONS

Sethuraman, Vijay A. et al., "pH-Responsive Sulfonamide/PEI System for Tumor Specific Gene Delivery: An in Vitro Study", Biomacromolecules, vol. 7, 2006, pp. 64-70.

Sullenger "Emerging Clinical Applications of Nucleic Acids", The Journal of Clinical Investigation, 106(8):921-922 (2000).

Takahashi, et al., "Transgene Delivery of Plasmid DNA to Smooth Muscle Cells and Macrophages from a Biostable Polymer-Coated Stent", Gene Therapy, 10:1471-1478 (2003).

Thomas, et al., "Cross-linked Small Polyethylenimines: While Still Nontoxic, Deliver DNA Efficiently to Mammalian Cells in Vitro and in Vivo", Pharmaceutical Research, 22(3):373-380 (2005).

Thomas, et al., "Enhancing Polyethylenimine's Delivery of Plasmid DNA into Mammalian Cells", PNAS, 99(23):14640-14645 (2002).

Thomas, et al., "Full Deacylation of Polyethylenimine Dramatically Boosts its Gene Delivery Efficiency and Specificity to mouse lung", PNAS, 102(16):5679-5684 (2005).

Thomas, et al., "Non-Viral Gene Therapy: Polycation-Mediated DNA Delivery", Appl. Microbiol. Biotechnol., 62:27-34 (2003).

Urban-Klein, et al., "RNAi-Mediated Gene-Targeting Through Systemic Application of Polyethylenimine (PEI)-Complexed siRNA in vivo", Gene Therapy, 12:461-466 (2005).

Wieland, et al., "Non-Viral Vector Delivery from PEG-Hyaluroic Acid Hydrogels", Journal of Controlled Release, 120(3):233-241 (2007).

File History, for related U.S. Appl. No. 12/353,792, "Devices and Methods for Elution of Nucleic Acid Delivery Complexes," (306 pages), (Jul. 2014).

File History, for related U.S. Appl. No. 12/437,287, "Delivery of Nucleic Acid Complexes from Particles," (303 pages), (Jul. 2014).

Kapoor, M., "How to Cross-link Proteins", Cellular, Molecular and Microbial Biology Division, University of Calgary, pp. 1-6, (1996).

Zaitsev, et al., "Polyelectrolyte Nanoparticles Mediate Vascular Gene Delivery", Pharmaceutical Research, 21(9):1656-1661, (2004).

* cited by examiner

FUNCTIONALIZED POLYSACCHARIDES FOR ACTIVE AGENT DELIVERY

This application claims the benefit of U.S. Provisional Application No. 61/428,130, filed Dec. 29, 2010, the contents of which are herein incorporated by reference.

FIELD OF THE INVENTION

The present invention relates to polysaccharides. More specifically, the present invention relates to functionalized polysaccharides for active agent delivery and compositions and structures including the same.

BACKGROUND OF THE INVENTION

One promising approach to the treatment of various medical conditions is the administration of nucleic acids as a therapeutic agent. However, successful treatment with nucleic acids can depend on various aspects including site-specific delivery, stability during the delivery phase, and a substantial degree of biological activity within target cells. For various reasons, these steps can be difficult to achieve. In addition, formulation of compositions including nucleic acids remains a substantial challenge.

SUMMARY OF THE INVENTION

Embodiments of the invention include functionalized polysaccharides for active agent delivery and compositions and structures including the same. In an embodiment, the invention includes an active agent delivery composition including a polysaccharide functionalized with a coupling group, wherein the polysaccharide lacks charged groups at a pH of between 6 and 8; and a complex comprising a nucleic acid and a transfection agent.

In an embodiment, the invention includes an active agent delivery structure including a matrix comprising a polysaccharide covalently cross-linked through the residue of a coupling group on the polysaccharide, the polysaccharide lacking charged groups at a pH of between 6 and 8; and a nucleic acid delivery complex disposed within the active agent delivery structure, the nucleic acid delivery complex comprising a nucleic acid and a transfection agent.

In an embodiment, the invention includes a material for medical applications including glycogen functionalized with coupling groups at a degree of substitution of between about 0.01 and 0.5.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present invention is defined by the appended claims and their legal equivalents.

BRIEF DESCRIPTION OF THE FIGURES

The invention may be more completely understood in connection with the following drawings, in which.

While the invention is susceptible to various modifications and alternative forms, specifics thereof have been shown by way of example and drawings, and will be described in detail. It should be understood, however, that the invention is not limited to the particular embodiments described. On the contrary, the intention is to cover modifications, equivalents, and alternatives falling within the spirit and scope of the invention.

DETAILED DESCRIPTION OF THE INVENTION

As described above, embodiments of the invention include functionalized polysaccharides for active agent delivery and compositions and structures including the same. Conditions associated with processing of active agents, such as nucleic acids, can adversely impact the activity of the active agents in regard to transfection of cells. However, as shown herein, polysaccharides can be useful to maintain the activity of active agents such as nucleic acids. In addition, in various embodiments, polysaccharides can be functionalized with coupling groups, so as to allow for the formation of a cross-linked matrix of polysaccharides that include active agents such as nucleic acids therein. Various aspects of exemplary embodiments will now be described in greater detail.

Polysaccharides

Polysaccharides used with embodiments herein can be linear or branched polysaccharides. For example, branched polysaccharides can include those with alpha 1,6 glycosidic linkages. Exemplary polysaccharides can include pentose, and/or hexose subunits. Exemplary polysaccharides can specifically include, but are not limited to, alpha and beta glucans such as the alpha glucans dextran, glycogen, pullulan, amylose, amylopectin. Exemplary polysaccharides can further include dextrins including maltodextrins, and the like. Polysaccharides can also include gums such as pullulan, arabinose, galactan, etc. In some embodiments, the polysaccharide is a natural degradable polysaccharide. Further examples of polysaccharides are described in U.S. Publ. Pat. App. No. 2005/0255142 (Chudzik et al.), herein incorporated by reference in its entirety.

Polysaccharides can also include copolymers and/or terpolymers, and the like, that include saccharide and/or saccharide subunits and/or blocks.

In some embodiments, the polysaccharide can include other types of molecules. For example, similar to as in the case of glycogen, the polysaccharide can include a protein core.

While not intending to be bound by theory, it is believed that the use of polysaccharides lacking charged groups can offer advantages in the context of some embodiments herein. In some embodiments, the polysaccharide lacks charged groups at a pH of between 6 and 8.

Polysaccharides used with embodiments herein can have various molecular weights. By way of example, glycogen used with embodiments herein can have a molecular weight of greater than about 250,000. In some embodiments glycogen used with embodiments herein can have a molecular weight of between about 100,000 and 10,000,000 Daltons.

Refinement of the molecular weight of polysaccharides can be carried out using diafiltration. Diafiltration of polysaccharides such as maltodextrin can be carried out using ultrafiltration membranes with different pore sizes. As an example, use of one or more cassettes with molecular weight cut-off membranes in the range of about 1K to about 500 K can be used in a diafiltration process to provide polysaccharide preparations with average molecular weights in the range of less than 500 kDa, in the range of about 100 kDa to about 500 kDa, in the range of about 5 kDa to about 30 kDa, in the range of about 30 kDa to about 100 kDa, in the range of about 10 kDa to about 30 kDa, or in the range of about 1 kDa to about 10 kDa.

It will be appreciated that polysaccharides such as maltodextrin and amylose of various molecular weights are commercially available from a number of different sources. For example, Glucidex™ 6 (ave. molecular weight ~95,000 Da) and Glucidex™ 2 (ave. molecular weight ~300,000 Da) are available from Roquette (France); and MALTRIN™ maltodextrins of various molecular weights, including molecular weights from about 12,000 Da to 15,000 Da are available from GPC (Muscatine, Iowa).

Functionalization of Polysaccharides

In various embodiments herein, polysaccharides are functionalized with one or more coupling groups to facilitate a plurality of polysaccharides to be coupled together in a linear or branched manner. In some embodiments, the coupling group is an ethylenically unsaturated group. Suitable ethylenically unsaturated groups include, but are not limited to, vinyl groups, acrylate groups, methacrylate groups, ethacrylate groups, 2-phenyl acrylate groups, acrylamide groups, methacrylamide groups, itaconate groups, and styrene groups. Combinations of different ethylenically unsaturated groups can be used.

In preparing the polysaccharide having pendent coupling groups any suitable synthesis procedure can be used. Suitable synthetic schemes typically involve reaction of, for example, hydroxyl groups on the polysaccharide, such as glycogen, amylose or maltodextrin. Synthetic procedures can be modified to produce a desired number of coupling groups pendent from the polysaccharide backbone. For example, the hydroxyl groups can be reacted with a coupling group-containing compound or can be modified to be reactive with a coupling group-containing compound. The number and/or density of acrylate groups can be controlled using the present method, for example, by controlling the relative concentration of reactive moiety to saccharide group content.

The amount of coupling group per polysaccharide can be described in terms of the degree of substitution (e.g., moles of coupling group per mole of polysaccharide). In various embodiments, the degree of substitution is greater than or equal to 0.01. In some embodiments, the degree of substitution is greater than or equal to 0.02. In some embodiments, the degree of substitution is greater than or equal to 0.05. In some embodiments, the degree of substitution is greater than or equal to 0.1. In some embodiments, the degree of substitution is greater than or equal to 0.15. In some embodiments, the degree of substitution is less than or equal to 0.5. In some embodiments, the degree of substitution is less than or equal to 0.4. In some embodiments, the degree of substitution is less than or equal to 0.3. In some embodiments, the degree of substitution is less than or equal to 0.2. In some embodiments, the degree of substitution is between about 0.01 and 0.5.

The amount of coupling group can be, for example, about 0.01 µmoles of coupling group per milligram of polysaccharide (0.01 µmoles/mg) or greater. In some embodiments, the amount of coupling group can be at least about 0.05 µmoles of coupling group per milligram of polysaccharide. In some embodiments, the amount of coupling group can be from about 0.01 µmol/mg to about 0.5 µmol/mg. In some embodiments, the amount of coupling group can be from about 0.05 µmol/mg to about 0.5 µmol/mg.

The amount of coupling groups on the polysaccharide can affect polysaccharide crosslinking in the matrix. A more highly crosslinked matrix can be more impervious to degradation by enzymes, and can therefore provide a slower rate of degradation, resulting in slower bioactive agent release and degradation product degradation. A more highly crosslinked matrix can be useful for implantable articles which deliver bioactive agent for long periods of time, such as greater than about three months, or greater than about six months. A less crosslinked matrix can be useful for implantable articles that deliver bioactive agent for shorter periods of time, such as less than about three months.

It will be appreciated that polysaccharides can also be functionalized with groups other than, or in addition to, pendent coupling groups. By way of example, saccharides can be derivatized with hydrophobic pendent groups.

Further examples of the functionalization of polysaccharides are described in U.S. Publ. Pat. App. No. 2005/0255142 (Chudzik et al.), herein incorporated by reference in its entirety.

Cross-Linking Initiators

As used herein, an "initiator" refers to a compound, or more than one compound, that is capable of promoting the formation of a reactive species from the coupling group. For example, the initiator can promote a free radical reaction of natural biodegradable polysaccharide having a coupling group. In one embodiment the initiator is a photoreactive group (photoinitiator) that is activated by radiation. In some embodiments, the initiator can be an "initiator polymer" that includes a polymer having a backbone and one or more initiator groups pendent from the backbone of the polymer.

In some aspects the initiator is a compound that is light sensitive and that can be activated to promote the coupling of the polysaccharide via a free radical polymerization reaction. These types of initiators are referred to herein as "photoinitiators." In some aspects it is preferred to use photoinitiators that are activated by light wavelengths that have no or a minimal effect on a bioactive agent if present in the composition. A photoinitiator can be present in a sealant composition independent of the amylose polymer or pendent from the amylose polymer.

In some embodiments, photoinitiation occurs using groups that promote an intra- or intermolecular hydrogen abstraction reaction. This initiation system can be used without additional energy transfer acceptor molecules and utilizing non-specific hydrogen abstraction, but is more commonly used with an energy transfer acceptor, typically a tertiary amine, which results in the formation of both aminoalkyl radicals and ketyl radicals. Examples of molecules exhibiting hydrogen abstraction reactivity and useful in a polymeric initiating system, include analogs of benzophenone, thioxanthone, and camphorquinone. Further examples of photoinitiators are described in U.S. Pat. No. 6,077,698.

In some aspects the photoinitiator is a compound that is activated by long-wavelength ultraviolet (UV) and visible light wavelengths. For example, the initiator includes a photoreducible or photo-oxidizable dye. Photoreducible dyes can also be used in conjunction with a compound such as a tertiary amine. The tertiary amine intercepts the induced triplet producing the radical anion of the dye and the radical cation of the tertiary amine. Examples of molecules exhibiting photosensitization reactivity and useful as an initiator include acridine orange, camphorquinone, ethyl eosin, eosin Y, erythrosine, fluorescein, methylene green, methylene blue, phloxime, riboflavin, rose bengal, thionine, and xanthine dyes.

Thermally reactive initiators can also be used to promote the polymerization of natural biodegradable polymers having pendent coupling groups. Examples of thermally reactive initiators include 4,4'-azobis(4-cyanopentanoic acid), 2,2-azobis[2-(2-imidazolin-2-yl)propane]dihydrochloride, and analogs of benzoyl peroxide. Redox initiators can also be used to promote the polymerization of the natural biodegradable polymers having pendent coupling groups. In general, combinations of organic and inorganic oxidizers, and organic and inorganic reducing agents are used to generate radicals for polymerization. A description of redox initiation can be found in *Principles of Polymerization,* 2nd Edition, Odian G., John Wiley and Sons, pgs 201-204, (1981).

The matrix can also be formed using an initiator that includes an oxidizing agent/reducing agent pair, a "redox pair," to drive polymerization of the biodegradable polysaccharide. In this case, polymerization of the polysaccharide is carried out upon combining one or more oxidizing agents with one or more reducing agents. Other compounds can be included in the composition to promote polymerization of the polysaccharides.

In order to promote polymerization of the polysaccharides in a composition to form a matrix, the oxidizing agent is added to the reducing agent in the presence of the one or more polysaccharides. For example, a composition including a polysaccharide and a reducing agent is added to a composition including an oxidizing agent, or a composition including a polysaccharide and an oxidizing agent is added to a composition containing a reducing agent. One desirable method of preparing a matrix is to combine a composition including a polysaccharide and an oxidizing agent with a composition including a polysaccharide and a reducing agent.

The oxidizing agent can be selected from inorganic or organic oxidizing agents, including enzymes; the reducing agent can be selected from inorganic or organic reducing agents, including enzymes. Exemplary oxidizing agents include peroxides, including hydrogen peroxide, metal oxides, and oxidases, including glucose oxidase. Exemplary reducing agents include salts and derivatives of electropositive elemental metals such as Li, Na, Mg, Fe, Zn, Al, and reductases. In one mode of practice, the reducing agent is present at a concentration of about 2.5 mM or greater when the reducing agent is mixed with the oxidizing agent. Prior to mixing, the reducing agent can be present in a composition at a concentration of, for example, 5 mM or greater.

Other reagents can be present in the composition to promote polymerization of the biodegradable polysaccharide. Other polymerization promoting compounds can be included in the composition, such as metal or ammonium salts of persulfate.

Optionally, the compositions and methods of the invention can include polymerization accelerants that can improve the efficiency of polymerization. Examples of useful accelerants include N-vinyl compounds, particularly N-vinyl pyrrolidone and N-vinyl caprolactam. Such accelerants can be used, for instance, at a concentration of between about 0.01% and about 5%, and preferably between about 0.05% and about 0.5%, by weight, based on the volume of the matrix-forming composition.

Nucleic Acids

Nucleic acids used with embodiments of the invention can include various types of nucleic acids that can function to provide a therapeutic effect. Exemplary types of nucleic acids can include, but are not limited to, ribonucleic acids (RNA), deoxyribonucleic acids (DNA), small interfering RNA (siRNA), micro RNA (miRNA), piwi-interacting RNA (piRNA), short hairpin RNA (shRNA), antisense nucleic acids, aptamers, ribozymes, locked nucleic acids and catalytic DNA.

Transfection Agents

Exemplary transfection agents used with embodiments of the invention can include those compounds that can be complexed with nucleic acids in order to preserve the activity of the nucleic acid and transfection agent complexes during the manufacturing and delivery processes. Exemplary transfection agents can also include those that can promote intracellular delivery of the nucleic acid. As such, transfection agents can enhance therapeutic uses of nucleic acids as administered to subjects.

Exemplary classes of suitable transfection agents can include both cationic compounds (compounds having a net positive charge) and charge neutral compounds. By way of example, suitable transfection agents can include cationic and non-cationic polymers and cationic and non-cationic lipids. Exemplary cationic lipids can include, but are not limited to, 3β-[N-(N',N'-dimethylaminoethane)-carbamoyl]cholesterol hydrochloride (DC-cholesterol); 1,2-dioleoyl-3-trimethylammonium-propane (DOTAP); dimethyldioctadecylammonium (DDAB); 1,2-dioleoyl-sn-glycero-3-ethylphosphocholine (EPC); 1,2-di-O-octadecenyl-3-trimethylammonium propane (DOTMA); 1,2-di-(9Z-octadecenoyl)-3-dimethylammonium-propane (DODAP); 1,2-dilinoleyloxy-3-dimethylaminopropane (DLinDMA) and derivatives thereof. Exemplary helper or fusogenic lipids can include, but are not limited to, 1,2-dioleoyl-sn-glycero-3-phosphoethanolamine (DOPE); cholesterol; 1,2-dioctadecanoyl-sn-glycero-3-phosphocholine (DSPC); 1,2-distearoyl-sn-glycero-3-phosphoethanolamine (DSPE). Other exemplary lipids can include, but are not limited to, lipidoids, atuplex formulations, and PEGylated forms of lipids described above. In some cases a mixture of lipids can be used form complexes.

Suitable transfection agents can also include polycation containing cyclodextrin, histones, cationized human serum albumin, aminopolysaccharides such as chitosan, peptides such as poly-L-lysine, poly-L-ornithine, and poly(4-hydroxy-L-proline ester, and polyamines such as polyethylenimine (PEI), polypropylenimine, polyamidoamine dendrimers, and poly(beta-aminoesters).

Transfection agents can also include peptides, such as those that include a nucleic acid binding domain and a nuclear localization domain in order to form a peptide-nucleic acid delivery construct. As used herein, the term "peptide" shall include any compound containing two or more amino-acid residues joined by amide bond(s) formed from the carboxyl group of one amino acid (residue) and the amino group of the next one. As such, peptides can include oligopeptides, polypeptides, proteins, and the like. It will be appreciated that many different peptides are contemplated herein. One exemplary peptide, known as MPG, is a 27 amino acid bipartite amphipathic peptide composed of a hydrophobic domain derived from HIV-1 gp41 protein and a basic domain from the nuclear localization sequence (NLS) of SV40 large T antigen (commercially available as the N-TER Nanoparticle siRNA Transfection System from Sigma-Aldrich, St. Louis, Mo.). Another exemplary peptide, known as MPGΔ$^{NLS}$, is also a 27 amino acid bipartite amphipathic peptide. Other exemplary peptides can include poly-arginine fusion peptides. Still other exemplary peptides include those with protein transduction domains linked with a double-stranded RNA binding domain.

Other transfection agents can include solid nucleic acid lipid nanoparticles (SNALPs), liposomes, protein transduction domains, polyvinyl pyrrolidone (PVP), peptides (including oligopeptides, polypeptides, proteins), and the like. Additionally, transfection agents may also be conjugated to molecules which allow them to target specific cell types. Examples of targeting agents include antibodies and peptides which recognize and bind to specific cell surface molecules.

Complex Formation

Complexes can be formed from transfection agents and nucleic acids through various processes. In some cases, for example, a cationic transfection agent interacts with an anionic nucleic acid molecule and condenses into a compact, ordered complex. As such, in some embodiments, the nucleic acid can simply be contacted with the transfection agent in order to form a complex between the nucleic acid and the transfection agent.

Nucleic acids complexed with a transfection agent including a lipid, lipidoid, or other molecule of an amphipathic nature can exist in at least two structurally distinct forms, a lipoplex or a liposome.

As used herein, the term "lipoplex" shall refer to an artificial vesicle consisting of a micelle (an aggregate of amphipathic molecules oriented with hydrophobic moieties pointed inward and polar groups pointing outwards) or lipid bilayer, with siRNA coating the exterior and interfacing with the polar groups of the molecules that make up the micelle or lipid bilayer.

As used herein, the term "liposome" shall refer to an artificial vesicle consisting of a continuous bilayer or multibilayer of lipids enclosing some of the nucleic acid active agent within the liposome.

Although lipoplexes and liposomes can frequently include the same components, their substantially differing structure can result from the preparation techniques used. Formation techniques for liposomes can include passive encapsulation, ethanol drop encapsulation, encapsulation of nucleic acid in ethanol destabilized liposomes, reverse-phase evaporation encapsulation and spontaneous vesicle formation by ethanol dilution to form stable nucleic acid lipid particles (SNALPs) (techniques reviewed in MacLachlan I. Liposomal formulations for nucleic acid delivery. In: Crooke ST, editor. Antisense Drug Technology: Principles, Strategies, and Applications. Boca Raton (FL): CRC Press; 2008. p. 237-70).

In contrast, to form lipoplexes, typically a liposome or micelle is formed first, and then a nucleic acid such as siRNA is complexed to the outer surface of the liposome or micelle. For example, DOTAP (as merely one non-limiting example of a transfection agent) can first be formulated as micelles in distilled deionized water before reacting with siRNA. In one approach, the ethanol of the DOTAP solution is first evaporated on a rotovap forming a film of DOTAP. Then, using sonication, DOTAP is dissolved in distilled deionized water forming nano-size micelles. Subsequent reaction with siRNA can then form lipoplexes, where siRNA coats the outside of the micelles. It will be appreciated, however, that other approaches to the formation of lipoplexes and liposomes can be used.

In some embodiments, the amount of polysaccharide is relatively small in comparison to the amount of nucleic acid and transfection agent. By way of example in some embodiments, the wt./wt. ratio of polysaccharide to the nucleic acid and transfection agent is less than or equal to 25 to 1. In some embodiments, the wt./wt. ratio of polysaccharide to the nucleic acid and transfection agent is less than or equal to 15 to 1. In some embodiments, the wt./wt. ratio of polysaccharide to the nucleic acid and transfection agent is less than or equal to 10 to 1. In some embodiments, the wt./wt. ratio of polysaccharide to the nucleic acid and transfection agent is less than or equal to 5 to 1.

Particle Formation

It will be appreciated that formation of particles, such as microparticles, in accordance with embodiments herein can include various steps including one or more of contacting, combining, mixing, dispersing, sonicating, forming, extracting, removing solvents, drying, lyophilization, and the like. In some embodiments, a nucleic acid solution can be contacted with a transfection agent solution in order to form a combined reagent solution. In some embodiments, the transfection agent solution can be treated first so as to form micelles before being contacted with the nucleic acid solution. In some embodiments, other components such as polymers and/or excipients can also be added to the nucleic acid solution, the transfection agent solution, or after combination to the combined reagent solution.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

The present invention may be better understood with reference to the following examples. These examples are intended to be representative of specific embodiments of the invention, and are not intended as limiting the scope of the invention.

EXAMPLES

Example 1

Synthesis of Glycogen-Methacrylate 1-methylimidazole (Sigma-Aldrich) and methacrylic anhydride (Fluka) were purchased through Sigma Aldrich (St. Louis, Mo.). Dimethylsulfoxide (Alfa Aesar), glycogen (Spectrum), and dialysis tubing (Spectrum Labs) were purchased through VWR International.

Figure 1:
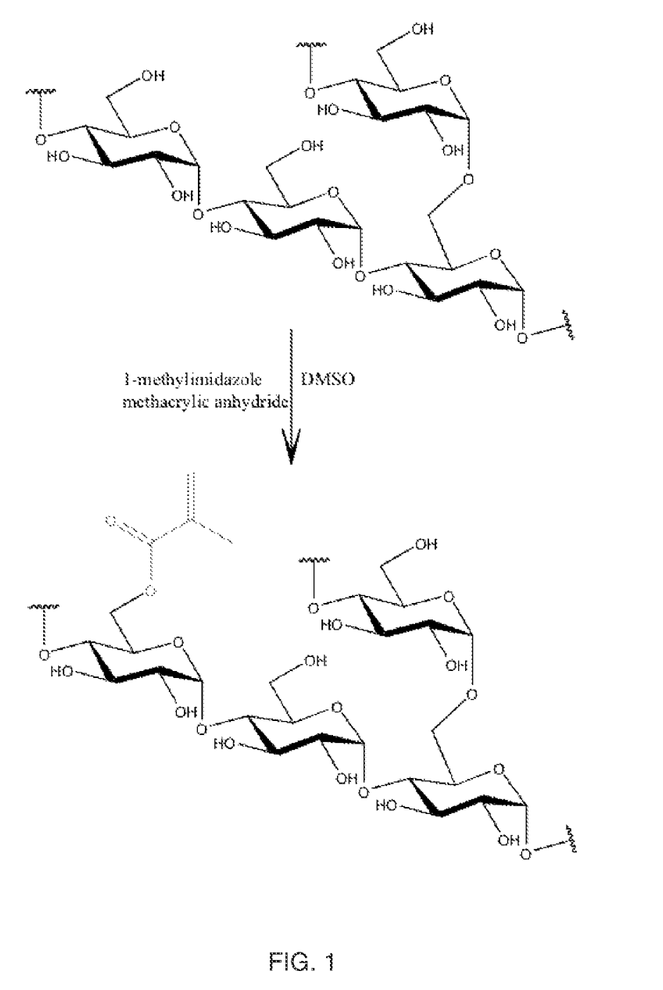
FIG. 1 shows a reaction diagram for functionalizing glycogen with a coupling group.

Methacrylation was performed at a degree of substitution of (D.S) 0.05, 0.1 or 0.15; and methacrylate groups were coupled via ester linkages pursuant to the following procedure (the specific amounts of reagents being specific for D.S. 0.1). Into a dry amber vessel, glycogen (shellfish-derived glycogen, MW~$1.10^6$ Da, 5.00 g, 30.84 mmol) was weighed and dissolved into anhydrous dimethylsulfoxide (DMSO) (50.0 mL). The solution was heated to 50° C. in order to fully solubilize the glycogen. Once all material was in solution, the methacrylic anhydride (459 uL, 3.08 mmol) was weighed and added to the reaction vessel and stirred magnetically. Next, the 1-methylimidazole (367 uL, 4.62 mmol) was added to the vessel. All reagents stirred magnetically overnight at room temperature. FIG. 1 shows a reaction diagram for this process. Following reaction, the solution was transferred into SpectraPor7 MWCO 1000 dialysis tubing to remove impurities and unreacted starting materials. The product dialyzed in deionized water for 48 hours under constant flow. The sample was then removed from the tubing and placed into a lyophilizer to freeze-dry into a fluffy white powder. The methacrylated glycogen was analyzed for methacrylate load by $^1$H NMR and determined to be 0.071 mmol methacrylate/g polymer (or μmol/mg). The yield was 84%.

Example 2

Crosslinking of Glycogen Methacrylate Microparticles

Ethylenebis (4-benzoylbenzyldimethylammonium)dibromide (IUPAC-N1,N2-bis(4-benzoylbenzyl)-N1,N1,N2,N2-tetramethylethane-1,2-diaminium bromide) as described in U.S. Pat. No. 5,714,360 (herein incorporated by reference) was obtained.

Figure 2A:
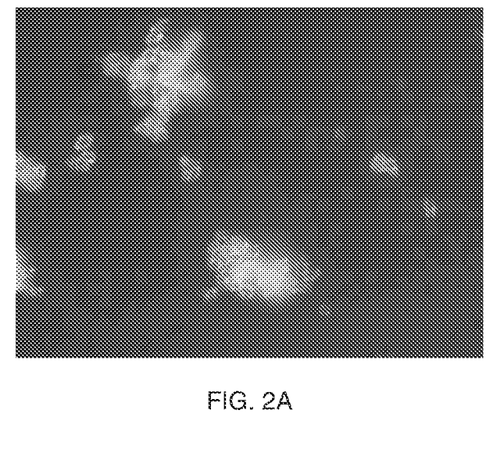
FIG. 2A is an image taken with polarized light microscopy at 500× magnification of particles formed in accordance with embodiments herein.
Figure 2B:
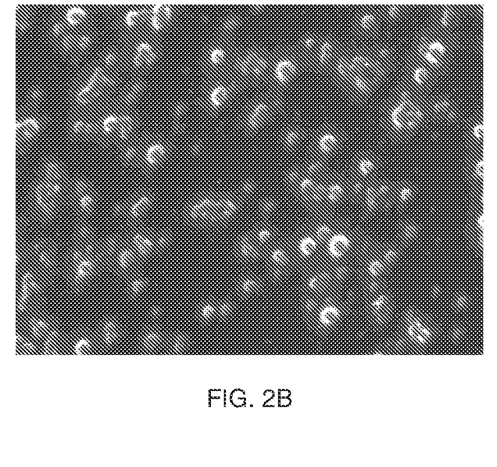
FIG. 2B is an image taken with dark field microscopy at 500× magnification of particles formed in accordance with embodiments herein.

To 10 ml of a solution of PEG 20 kDa at 300 mg/ml in water 5 mg of ethylenebis (4-benzoylbenzyldimethylammonium) dibromide in 50 ul acetone was added. Glycogen-methacrylate at a degree of substitution (D.S.) of 0.15 in water was dissolved at a) 10 mg/ml, or b) 20 mg/ml. The PEG/ethylenebis (4-benzoylbenzyldimethylammonium) dibromide solution was added to the glycogen-methacrylate solutions at a) 10:3 or b) 5:2 glycogen/PEG ratio resulting in a phase-separation of the glycogen solution. The phase separated mixtures were subsequently UV-irradiated for 3 minutes in a cold room yielding crosslinked particles. The formed particles were spun and washed with water and did not redissolve. FIG. 2A is an image taken with polarized light microscopy at 500× magnification of the particles. FIG. 2B is an image taken with dark field microscopy at 500× magnification of the particles.

Example 3

Glycogen-Methacrylate Providing siRNA/DOTAP Lipoplex Stability

Using both anti-luciferase and scrambled (non-coding) siRNA, siRNA/DOTAP complexes were made with 10 μg siRNA quantities and 100 ug DOTAP. DOTAP micelles in water were obtained by evaporating 5 ml of a DOTAP solution at 20 mg/ml in ethanol (Avanti Polar Lipids, Ala.) in a round bottom flask until a dry film was obtained. DOTAP was resuspended in 100 ml water using ultrasonication yielding a 1 mg/ml suspension. 35 μl siRNA at 20 μM (10 μg) was diluted in 65 μL water. 100 μL DOTAP suspension at 1 mg/mL was added and mixed by pipetting up and down. Glycogen or glycogen-methacrylate at a degree of substitution (D.S.) of 0.05, 0.1 or 0.15 were dissolved in water at 5 mg/ml containing ethylenebis (4-benzoylbenzyldimethylammonium)dibromide at 0.5 mg/mL and sterile-filtered through a 0.2 μm syringe filter.
Glycogen or Glycogen-methacrylate solutions were added as follows:
  A. 'no excip': none added
  B. 58 μL (1:3 ratio complex vs excipient)
  C. 116 μL (1:5 ratio complex vs excipient)
The samples were split into 3 parts. One was kept for control, two were lyophilized.

After lyophilization one of the two lyophilized parts was suspended in 200 μL ethyl acetate and dried in vacuum. All samples were reconstituted in serum-free DMEM and further diluted in DMEM until siRNA was at 50 nM concentration and put on HR5CL11 cells to test for bioactivity.

100 μL of samples was added to 3 wells of a 96-well plate that was seeded with HR5CL11 cells at $10^5$ cell/ml and incubated for 24 hours prior to the transfection. After 3 hours of incubation the cell media was replaced with fresh DMEM/ 10% FBS/5 μg/ml dox and further incubated for 24 hours.

Figure 3:
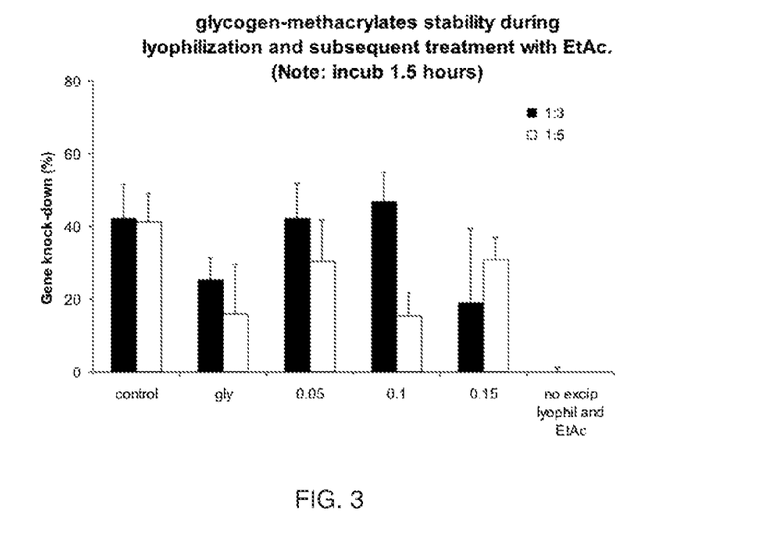
FIG. 3 is a graph showing gene knock down resulting from transfection with siRNA corresponding to various experimental conditions.

The cells were then incubated with Cell Titre Blue for 1.5 hours to assess any toxicity. All media was removed and cells were lysed using Glo lysis buffer. Luciferase content was measured by luminescence using the Bright-Glo luciferase assay. The raw data obtained from luciferase assay was normalized against the toxicity data by division and subsequent multiplication by 5000. The results are shown in FIG. 3. Gene knock-down is expressed as 100%−$RLU_{luc}$/ $RLU_{control}$*100%. RLU=relative light units.

Example 4

Glycogen-Methacrylate/siRNA/DOTAP Lipoplex Stability in Scaled-Up Batches

Using both anti-luciferase and scrambled (non-coding) siRNA, siRNA/DOTAP complexes were made with 1.25 mg siRNA quantities and 12.5 mg DOTAP. DOTAP micelles in water were obtained by evaporating 5 ml of a DOTAP solution at 20 mg/ml in ethanol (Avanti Polar Lipids, Ala.) in a round bottom flask until a dry film was obtained. DOTAP was resuspended 100 ml water using ultrasonication yielding a 1 mg/ml suspension. 88 μl siRNA at 1 mM (1.25 mg) was diluted in 12.5 mL water. 12.5 mL DOTAP suspension at 1 mg/mL was added and mixed by pipetting up and down.

Dextrose, glycogen, or glycogen-methacrylate at a degree of substitution (D.S.) of 0.1 was dissolved in water at 5 mg/ml sterile-filtered through a 0.2 μm syringe filter. 7.25 mL of excipient solution was added. The batches were lyophilized in petri-dishes. Remaining liquid in tubes were used as control. 200 μL from batches were taken in microtubes and lyophilized. All samples were reconstituted in serum-free DMEM and further diluted in DMEM until siRNA was at 50 nM concentration and put on HR5CL11 cells to test bioactivity. 100 μL of samples was added to 3 wells of a 96-well plate that was seeded with HR5CL11 cells at $10^5$ cell/ml and incubated for 24 hours prior to the transfection. After 3 hours of incubation the cell media was replaced with fresh DMEM/ 10% FBS/5 μg/ml doxycycline and further incubated for 24 hours.

Figure 4:
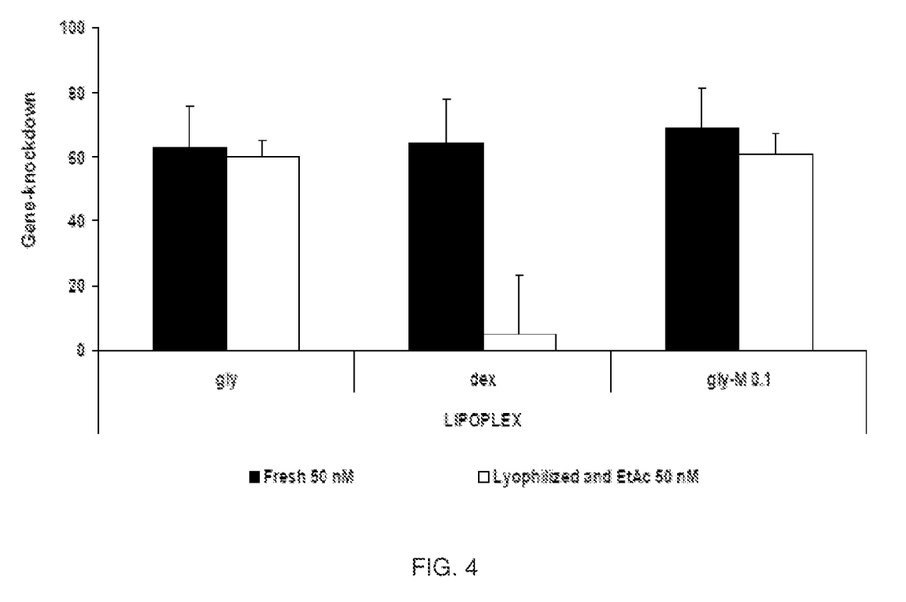
FIG. 4 is a graph showing gene knock down resulting from transfection with siRNA corresponding to various experimental conditions.

The cells were then incubated with Cell Titre Blue for 1.5 hours to assess any toxicity. All media was removed and cells were lysed using Glo-lysis buffer. Luciferase content was measured by luminescence using the Bright-Glo luciferase assay. The raw data obtained from luciferase assay was normalized against the toxicity data by division and subsequent multiplication by 5000. The results are shown in FIG. 4. Gene knock-down is expressed as 100%−$RLU_{luc}$/ $RLU_{control}$*100%. RLU=relative light units.

Example 5

Glycogen-Methacrylate Gels for siRNA Delivery

Using both anti-luciferase GL4 siRNA and scrambled (non-coding) siRNA, both liposomes and lipoplexes with DOTAP at 1:10 w/w ratio were made in duplicate.
  A) Liposome Preparation:
21 μL siRNA 1 mM (300 μg) was diluted in 1.5 mL water. 150 μL DOTAP 20 mg/mL in ethanol (30 mg DOTAP) was added and the mixture was sonicated for 10 minutes.

B) Lipoplex Preparation:

21 μL siRNA 1 mM (300 μg) was diluted in 6 mL water. 3 mL of a DOTAP suspension at 1 mg/mL in water was added and pipetted up and down several times.

To the batches 1.2 mL of a sterile-filtered glycogen-methacrylate D.S. 0.1 solution at 50 mg/mL in water was added totaling 60 mg of the glycogen-methacrylate. 750 μL ethylenebis (4-benzoylbenzyldimethylammonium)dibromide solution at 0.2 mg/mL in water was added to the resulting mixtures. Upon lyophilization the residues were reconstituted in 300 μL water. 6 times 50 μL of each batch was pipetted in a well of a clear 96-well plate and subsequently irradiated 2 times 1 minute by a Blue-wave UV lamp. 200 μL of 10 mM HEPES buffer was put on top of the soft gels. The plate was sealed and left at 37° C. for controlled release measurements. At specific time intervals the buffer was removed and replaced with fresh 10 mM HEPES.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

The invention claimed is:

1. An active agent delivery composition comprising
   a polysaccharide functionalized with a coupling group, wherein the polysaccharide lacks charged groups at a pH of between 6 and 8, wherein the degree of substitution is greater than or equal to 0.01 and less than or equal to 0.2; and
   a complex comprising a nucleic acid and a transfection agent.

2. The active agent delivery composition of claim 1, the polysaccharide comprising a branched polysaccharide.

3. The active agent delivery composition of claim 1, the polysaccharide comprising alpha 1,6 glycosidic linkages.

4. The active agent delivery composition of claim 1, further comprising a protein core, the polysaccharide contacting the protein core.

5. The active agent delivery composition of claim 1, the polysaccharide comprising glycogen or derivative thereof.

6. The active agent delivery composition of claim 1, the coupling group comprising an ethylenically unsaturated group.

7. The active agent delivery composition of claim 1, the coupling group comprising a methacrylate group.

8. The active agent delivery composition of claim 1, the nucleic acid comprising siRNA.

9. The active agent delivery composition of claim 1, the transfection agent comprising a cationic lipid.

10. The active agent delivery composition of claim 1, further comprising a crosslinking agent.

11. An active agent delivery structure comprising
    a matrix comprising a polysaccharide covalently crosslinked through the residue of a coupling group on the polysaccharide, the polysaccharide lacking charged groups at a pH of between 6 and 8, wherein the degree of substitution is greater than or equal to 0.01 and less than or equal to 0.2; and
    a nucleic acid delivery complex disposed within the active agent delivery structure, the nucleic acid delivery complex comprising a nucleic acid and a transfection agent.

12. The active agent delivery structure of claim 11, the polysaccharide comprising a branched polysaccharide.

13. The active agent delivery structure of claim 11, the polysaccharide comprising alpha 1,6 glycosidic linkages.

14. The active agent delivery structure of claim 11, further comprising a protein core, the polysaccharide contacting the protein core.

15. The active agent delivery structure of claim 11, the polysaccharide comprising glycogen or derivative thereof.

16. The active agent delivery structure of claim 11, the coupling group comprising an ethylenically unsaturated group.

17. The active agent delivery structure of claim 11, the coupling group comprising a methacrylate group.

18. The active agent delivery structure of claim 11, the nucleic acid comprising siRNA.

19. The active agent delivery structure of claim 11, further comprising a crosslinking agent.

20. The active agent delivery composition of claim 1, wherein the degree of substitution is less than or equal to 0.15.

* * * * *